(12) United States Patent
Kuma et al.

(10) Patent No.: US 10,696,627 B2
(45) Date of Patent: Jun. 30, 2020

(54) PROCESS FOR PRODUCING PENTAERYTHRITOL MERCAPTOCARBOXYLIC ACID ESTER, POLYMERIZABLE COMPOSITION, RESIN, OPTICAL MATERIAL, AND LENS

(71) Applicant: MITSUI CHEMICALS, INC., Minato-ku, Tokyo (JP)

(72) Inventors: Shigetoshi Kuma, Kurume (JP); Masayuki Furuya, Arao (JP); Takeshi Nishimura, Yanagawa (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 0 days.

(21) Appl. No.: 15/739,425

(22) PCT Filed: Jun. 24, 2016

(86) PCT No.: PCT/JP2016/068788
§ 371 (c)(1),
(2) Date: Dec. 22, 2017

(87) PCT Pub. No.: WO2016/208707
PCT Pub. Date: Dec. 29, 2016

(65) Prior Publication Data
US 2018/0186733 A1 Jul. 5, 2018

(30) Foreign Application Priority Data
Jun. 24, 2015 (JP) ................. 2015-126417

(51) Int. Cl.
*C07C 323/52* (2006.01)
*C07C 319/12* (2006.01)
*C08G 18/38* (2006.01)
*G02B 1/04* (2006.01)
*C07C 31/24* (2006.01)
*G01N 21/03* (2006.01)

(52) U.S. Cl.
CPC .......... *C07C 319/12* (2013.01); *C07C 31/245* (2013.01); *C07C 323/52* (2013.01); *C08G 18/38* (2013.01); *C08G 18/3876* (2013.01); *G01N 21/0303* (2013.01); *G02B 1/04* (2013.01); *G02B 1/041* (2013.01)

(58) Field of Classification Search
USPC ........................................................ 560/147
See application file for complete search history.

(56) References Cited

U.S. PATENT DOCUMENTS

| 4,329,519 A | 5/1982 | Werle et al. |
| 4,680,369 A | 7/1987 | Kajimoto et al. |
| 4,689,387 A | 8/1987 | Kajimoto et al. |
| 4,775,733 A | 10/1988 | Kanemura et al. |
| 4,780,522 A | 10/1988 | Kajimoto et al. |
| 7,569,736 B2 | 8/2009 | Bengtsson et al. |
| 2009/0062575 A1 | 3/2009 | Bengtsson et al. |
| 2009/0270583 A1 | 10/2009 | Kuma et al. |
| 2011/0065887 A1 | 3/2011 | Kuma et al. |
| 2011/0245531 A1* | 10/2011 | Kuma ................ C07C 319/12 560/147 |

FOREIGN PATENT DOCUMENTS

| CN | 101291907 A | 10/2008 |
| JP | 33-003869 B1 | 5/1958 |
| JP | 37-006503 B1 | 6/1962 |
| JP | 39-009071 B | 5/1964 |
| JP | 56-020530 A | 2/1981 |
| JP | 60-199016 A | 10/1985 |
| JP | 60-217229 A | 10/1985 |
| JP | 63-046213 A | 2/1988 |
| JP | 01-215293 A | 8/1989 |
| JP | 10-120646 A | 5/1998 |
| JP | 11-290089 A | 10/1999 |
| JP | 2012-188437 A | 10/2012 |
| WO | WO 2007/052329 A1 | 5/2007 |

OTHER PUBLICATIONS

Jian et al.: "Study on the Synthesis of Pentaerythritoltetrakis (2-mercaptoacetate)" China Academic Journal Electronic Publishing House, 2010 (3 pages including English abstract).
The First Office Action issued by the State Intellectual Property Office of People's Republic of China in corresponding Chinese Patent Application No. 201680033855.1 dated Dec. 27, 2018 (14 pages including partial English translation).
Walter T. Reichle, "Catalytic Reactions by Thermally Activated, Synthetic, Anionic Clay Minerals", Journal of Catalysis, 1985, pp. 547-557, vol. 94, No. 2.
International Search Report (PCT/ISA/210) dated Sep. 20, 2016, by the Japanese Patent Office as the International Searching Authority for International Application No. PCT/JP2016/068788.
Written Opinion (PCT/ISA/237) dated Sep. 20, 2016, by the Japanese Patent Office as the International Searching Authority for International Application No. PCT/JP2016/068788.

* cited by examiner

*Primary Examiner* — Monique R Peets

(74) *Attorney, Agent, or Firm* — Buchanan Ingersoll & Rooney PC

(57) ABSTRACT

A process for producing a pentaerythritol mercaptocarboxylic acid ester of the present invention includes: a step of reacting pentaerythritol with a mercaptocarboxylic acid, in which an absorbance of a 5 wt % aqueous solution of the pentaerythritol at a wavelength of 270 nm, which is measured using a quartz cell having an optical path length of 50 mm, is 0.07 or less.

6 Claims, No Drawings

PROCESS FOR PRODUCING PENTAERYTHRITOL MERCAPTOCARBOXYLIC ACID ESTER, POLYMERIZABLE COMPOSITION, RESIN, OPTICAL MATERIAL, AND LENS

TECHNICAL FIELD

The present invention relates to a process for producing a pentaerythritol mercaptocarboxylic acid ester, a polymerizable composition, a resin, an optical material, and a lens.

BACKGROUND ART

A plastic lens is lighter than an inorganic lens and is hard to break, and it is possible to perform dyeing thereon. Therefore, in recent years, the plastic lens has been rapidly widespread as a candidate material forming a spectacle lens, a camera lens, and the like.

In addition, higher performance has been required for a resin for a plastic lens, and high refractive index, high Abbe number, low specific gravity, and high heat resistance have been required. Various resin materials for a lens have been developed and used so far.

Among them, technological development on a polyurethane resin has been actively performed, and the present inventors have also performed various kinds of technological development on a plastic lens in which this polyurethane resin is used (for example, refer to Patent Document 1, Patent Document 2, and Patent Document 3).

An example of a representative resin among them is a resin obtained by reacting a pentaerythritol mercaptocarboxylic acid ester with a polyiso(thio)cyanate compound. This resin is colorless and transparent, and has characteristics of high refractive index and low dispersion. This resin is one of the most suitable resins for a plastic lens having excellent impact resistance, dyeability, workability, and the like.

The pentaerythritol mercaptocarboxylic acid ester is produced through a so-called direct esterification method that a ordinal polyhydric alcohol is reacted with a ordinal mercaptocarboxylic acid in the presence of an esterification catalyst, while distilling off water, which is produced as a by-product outside a system (refer to Patent Document 4).

Pentaerythritol which is a raw material of this ester compound is usually produced by condensing acetaldehyde and formaldehyde. The purity of pentaerythritol is usually about 90 wt % and pentaerythritol contains several kinds of impurities. Among them, an example thereof includes bispentaerythritol which is a bi-molecular condensate of formaldehyde of pentaerythritol. If the content of this bispentaerythritol is greater than 5 wt %, it is known that there is a possibility that problems such as difficulty in performing release from a mold after completion of polymerization with a polyisocyanate compound or generation of bubbles in the obtained lens may be caused (refer to Patent Documents 5 and 6).

In addition, it is known that a pentaerythritol mercaptocarboxylic acid ester can be obtained which does not become cloudy even when reacted with poly(iso)thiocyanate, by controlling the content of alkali metal and alkaline earth metal to be a specific amount or less with respect to pentaerythritol used as a raw material (refer to Patent Document 7).

RELATED DOCUMENT

Patent Document

[Patent Document 1] Japanese Unexamined Patent Publication No. S60-199016

[Patent Document 2] Japanese Unexamined Patent Publication No. S60-217229

[Patent Document 3] Japanese Unexamined Patent Publication No. S63-46213

[Patent Document 4] Japanese Examined Patent Publication No. S39-9071

[Patent Document 5] Japanese Examined Patent Publication No. S56-20530

[Patent Document 6] Japanese Unexamined Patent Publication No. H10-120646

[Patent Document 7] International Publication No. 2007/052329

SUMMARY OF THE INVENTION

Technical Problem

When methods in the related arts disclosed in Patent Documents 1 to 7 are used, it is possible to obtain a resin in which occurrence of coloration or striae is suppressed to some extent and to produce a plastic lens using this resin.

However, in recent years, it has been necessary to further improve the appearance characteristics and the like of an optical material such as a plastic lens.

Here, in order to improve the appearance characteristics of an optical material, improvement through adding a modifier, adjusting polymerization conditions, or the like, for example, in a stage of obtaining a resin through polymerization has been considered.

However, it is concerned that in these methods, other physical properties are impaired by adding a modifier or the process efficiency is decreased by adjusting the polymerization conditions, or the like.

For this reason, it is considered preferable to improve a raw material itself to contribute to polymerization in obtaining a resin.

In view of such circumstances, an object of the present invention is to provide a process for producing a pentaerythritol mercaptocarboxylic acid ester which allows a colorless and transparent resin molded product which has an excellent appearance such as a color to be obtained.

Solution to Problem

The present inventors have conducted extensive studies in order to solve the above-described problems, and as a result, they have found that a color or the like of a resin molded product to be obtained is improved by managing pentaerythritol which is a raw material of a pentaerythritol mercaptocarboxylic acid ester so as to satisfy a specific absorbance.

That is, they have found that it is possible to stably produce a colorless and transparent resin molded product, which has an excellent appearance such as a color, by using specific pentaerythritol and have completed the invention.

That is, the present invention can be shown as follows.

[1] A process for producing a pentaerythritol mercaptocarboxylic acid ester, comprising: a step of reacting pentaerythritol with a mercaptocarboxylic acid to obtain a pentaerythritol mercaptocarboxylic acid ester, in which an absorbance of a 5 wt % aqueous solution of the pentaerythritol at a wavelength of 270 nm, which is measured using a quartz cell having an optical path length of 50 mm, is 0.07 or less.

[2] The process for producing a pentaerythritol mercaptocarboxylic acid ester according to [1], in which the absorbance is 0.003 or more.

[3] The process for producing a pentaerythritol mercaptocarboxylic acid ester according to [1] or [2], in which the mercaptocarboxylic acid is a 3-mercaptopropionic acid or a thioglycolic acid.

[4] A polymerizable composition including: the pentaerythritol mercaptocarboxylic acid ester obtained through the production method according to any one of [1] to [3]; and a polyiso(thio)cyanate compound.

[5] A resin obtained by curing the polymerizable composition according to [4].

[6] An optical material composed of the resin according to [5].

[7] A lens composed of the resin according to [5].

[8] A method for screening pentaerythritol, in a process for producing a pentaerythritol mercaptocarboxylic acid ester by reacting pentaerythritol with a mercaptocarboxylic acid, comprising: preparing a 5 wt % aqueous solution of the pentaerythritol; and selecting the pentaerythritol that an absorbance of the 5 wt % aqueous solution thereof at a wavelength of 270 nm, which is measured using a quartz cell having an optical path length of 50 mm, is 0.07 or less.

Advantageous Effects of Invention

In the present invention, it is possible to improve the appearance, such as a color, of a resin molded product to be obtained, by managing pentaerythritol which is a raw material of a pentaerythritol mercaptocarboxylic acid ester so as to satisfy a specific absorbance.

Furthermore, it is possible to obtain a resin of which the quality such as optical properties is also excellent using the pentaerythritol mercaptocarboxylic acid ester obtained through this method.

DESCRIPTION OF EMBODIMENTS

Hereinafter, the present invention will be described based on the following embodiment.

Unless otherwise specified, "a lower value to upper value" in the present specification represents a range being the lower value or more and the upper value or less.

(Process for Producing Pentaerythritol Mercaptocarboxylic Acid Ester)

First, a process for producing a pentaerythritol mercaptocarboxylic acid ester according to the present embodiment will be described.

The process for producing a pentaerythritol mercaptocarboxylic acid ester of the present embodiment includes a step of reacting pentaerythritol satisfying the following condition with a mercaptocarboxylic acid.

The absorbance of a 5 wt % aqueous solution of the pentaerythritol at a wavelength of 270 nm, which is measured using a quartz cell having an optical path length of 50 mm, is 0.07 or less.

That is, in the process for producing a pentaerythritol mercaptocarboxylic acid ester of the present embodiment, in a case where the 5 wt % aqueous solution of the pentaerythritol is prepared and the absorbance is measured using a quartz cell having an optical path length of 50 mm, pentaerythritol of which the absorbance at a wavelength of 270 nm is a specific value is used as a raw material.

In the present specification, in a case where the "pentaerythritol", the "mercaptocarboxylic acid", the "pentaerythritol mercaptocarboxylic acid ester", and the like contain impurities, these can be respectively described as a "pentaerythritol composition", a "mercaptocarboxylic acid composition", and a "pentaerythritol mercaptocarboxylic acid ester composition".

Hereinafter, each raw material used in the process for producing a pentaerythritol mercaptocarboxylic acid ester of the present embodiment will be described.

(Pentaerythritol)

In the present embodiment, in a case where a 5 wt % aqueous solution of pentaerythritol is prepared and the absorbance of the aqueous solution is measured using a quartz cell having an optical path length of 50 mm, pentaerythritol of which the absorbance at a wavelength of 270 nm is 0.07 or less is used. When the pentaerythritol satisfies the above-described numerical value, it is possible to improve the appearance, such as a color, of a resin molded product.

Here, this wavelength of 270 nm is not a wavelength corresponding to a so-called visible region, and a substance itself contributing to the value of the absorbance at this wavelength of 270 nm does not change optical characteristics of a resin molded product in the visible region. However, the present inventors have found that the substance contributing to the value of the absorbance at this wavelength of 270 nm brings about a certain kind of interaction when a resin is obtained through polymerization and affects optical characteristics or the like as a resin molded product to be obtained.

That is, the present inventors have found that it is important to manage pentaerythritol used as a raw material so as to satisfy the above-described value in order to ensure the quality of the pentaerythritol used as a raw material and that the management of the pentaerythritol can solve the problems of the present application.

In addition, regarding the pentaerythritol used in the process for producing a pentaerythritol mercaptocarboxylic acid ester of the present embodiment, the absorbance of a 5 wt % pentaerythritol aqueous solution at a wavelength of 270 nm may be preferably set to be 0.06 or less, more preferably set to be 0.055 or less, still more preferably set to be 0.035 or less, and particularly preferably set to be 0.015 or less.

By satisfying such a value, it is possible to further improve the appearance, such as a color, of a resin molded product to be obtained.

Here, when measuring the absorbance at this wavelength of 270 nm, it is possible to employ the following conditions.

First, a 5 wt % of aqueous solution is prepared using pentaerythritol and a measurement sample is prepared by filtering this aqueous solution. The absorbance of this measurement sample at a wavelength of 270 nm is obtained by filling a quartz cell having an optical path length of 50 mm with the measurement sample.

When measuring this absorbance, it is possible to use a spectrophotometer (equipment name: UV-1600) manufactured by Shimadzu Corporation.

In addition, regarding the pentaerythritol used in the process for producing a pentaerythritol mercaptocarboxylic acid ester of the present embodiment, the absorbance of a 5 wt % pentaerythritol aqueous solution at a wavelength of 270 nm is preferably 0.003 or more, more preferably 0.005 or more, and still more preferably 0.01 or more.

In a case where the absorbance of the 5 wt % pentaerythritol aqueous solution at a wavelength of 270 nm is set to be the above-described values or more, it is unnecessary to perform excessive purification and it is possible to improve the process efficiency as a whole process. In this manner, it is possible to ensure the quality of a product to be obtained by improving the process efficiency as a whole.

In the present embodiment, it is possible to set the absorbance of the 5 wt % pentaerythritol aqueous solution at a wavelength of 270 nm to be within the above-described range by purifying the pentaerythritol.

An example of the purification method includes a purification method performed through crystallization after dissolving pentaerythritol in a solvent. In general, water is used as the solvent. Water to be used as the solvent may be distilled water or ion exchange water. In addition, before the crystallization of the pentaerythritol from the solution in which the pentaerythritol is dissolved, the pentaerythritol may be crystallized after treating the pentaerythritol solution using a specific treating agent. Examples of the treating agent include various adsorbents such as activated carbon, activated alumina, silica gel, and a molecular sieve, an ion exchange resin, and a chelate resin. The crystallization may be repeated plural times or may be performed plural times while changing the treating agent.

In some cases, the absorbance of a commercially available pentaerythritol or a produced pentaerythritol is within or out of the range of the present invention in the above-described measurement method. In such cases, it is also possible to screen and use pentaerythritol of which the absorbance is within the range in the present invention.

In addition, in pentaerythritol used in the present embodiment, the content of bispentaerythritol as an impurity is preferably a specific amount or less. For example, the content of bispentaerythritol with respect to the total weight of pentaerythritol may be preferably set to be 0.01 wt % to 7 wt %, more preferably set to be 0.1 wt % to 5 wt %, and still more preferably set to be 1 wt % to 5 wt %.

In the present embodiment, it is possible to further improve the appearance, such as a color, of a resin molded product to be obtained by using pentaerythritol of which the absorbance and the content of bispentaerythritol are within the above-described ranges.

In pentaerythritol used in the present embodiment, the content of metal as an impurity is preferably a specific amount or less. The total content of metal with respect to the total weight of pentaerythritol may be set to be less than 1 wt %.

In the present embodiment, it is possible to further improve the appearance, such as a color, of a resin molded product to be obtained by using pentaerythritol of which the absorbance and the content of metal are within the above-described ranges.

Examples of metal include alkali metals such as Li, Na, K, Rb, and Cs, alkaline earth metals such as Mg, Ca, Sr, and Ba, and Ti, V, Cr, Mn, Fe, Co, Ni, Cu, Zn, and the like. Specifically, alkali metals and alkaline earth metals, particularly metals in which the content of Na and Ca is controlled are desirable.

In a case where the content of bispentaerythritol and the total content of metal are within the above-described ranges, a resin molded product is easily released from a mold after completion of polymerization of a pentaerythritol mercaptocarboxylic acid ester to be obtained and a polyiso(thio)cyanate compound, and therefore, it is possible to suppress generation of bubbles in the obtained resin molded product.

Furthermore, in a case where the absorbance, the content of bispentaerythritol, and the total content of metal are within the above-described ranges, it is possible to further improve the appearance, such as a color, of the obtained resin molded product.

Subsequently, the mercaptocarboxylic acid used in the present embodiment will be described.

(Mercaptocarboxylic Acid)

Examples of the mercaptocarboxylic acid used in the present embodiment include a 3-mercaptopropionic acid, a 2-mercaptopropionic acid, a thioglycolic acid, a thiolactic acid, a thiomalic acid, and a thiosalicylic acid.

In the present embodiment, a 3-mercaptopropionic acid or a thioglycolic acid is preferable as this mercaptocarboxylic acid from the viewpoints of the heat resistance (Tg) of a resin to be obtained, the availability as a mercaptocarboxylic acid, the reactivity in producing a pentaerythritol mercaptocarboxylic acid ester, and the like.

Here, a mercaptocarboxylic acid in which the content of an intermolecular condensed thioester compound is controlled is preferably used as the mercaptocarboxylic acid of the present embodiment.

The intermolecular condensed thioester compound is a compound in which a mercapto group and a carboxyl group of a mercaptocarboxylic acid are condensed between molecules through thioester bonding and is a compound in which the intermolecular bonding is performed between two, three or more molecules. A compound in which a mercapto group and a carboxyl group are condensed between two molecules through thioester bonding is called an inter-bimolecular condensed thioester compound. For example, a thioester compound in which a 3-mercaptopropionic acid is condensed between two molecules is a 3-(3-mercaptopropanoylthio)propionic acid.

Specifically, in a case where the total area of a mercaptocarboxylic acid and an intermolecular condensed thioester compound thereof in high-performance liquid chromatography measurement is set to be 100%, when the content of an inter-bimolecular condensed thioester compound of the mercaptocarboxylic acid is 5% or less (area percentage), a color of a pentaerythritol mercaptocarboxylic acid ester produced using the mercaptocarboxylic acid tends to be colorless and transparent, which is preferable. In addition, a polymerizable composition before polymerization which is obtained by mixing this pentaerythritol mercaptocarboxylic acid ester with polyiso(thio)cyanate has a low viscosity, and the obtained resin tends to be a colorless and transparent resin of which cloudiness is suppressed.

From the viewpoint of the suppression of cloudiness, the content of the inter-bimolecular condensed thioester compound of the mercaptocarboxylic acid used in the present embodiment is preferably 0.01% to 5%, more preferably 0.01% to 3%, and still more preferably 0.01% to 1% by area percentage in high-performance liquid chromatography measurement.

The content of the inter-bimolecular condensed thioester compound shown in the present embodiment is measured, for example, through the following analysis method. A column Mightysil RP-18GP manufactured by KANTO KAGAKU is connected to high-performance liquid chromatography devices (LC-6A, SPD-10A, CTO-10A) manufactured by Shimadzu Corporation, an aqueous solution of 0.01 M $KH_2PO_4$/acetonitrile (40/60) is used as an eluent, and the content of the inter-bimolecular condensed thioester compound in the mercaptocarboxylic acid at a column temperature of 40° C., a flow rate of the eluent of 0.95 ml/minute, and a wavelength of 230 nm is analyzed. The content of the inter-bimolecular condensed thioester compound is represented by area percentage in the case where the total area of the mercaptocarboxylic acid and the intermolecular condensed thioester compound thereof in high-performance liquid chromatography measurement is set to be 100%.

In the present embodiment, it is possible to further improve the appearance, such as a color, of a resin molded product to be obtained, by using pentaerythritol of which the absorbance is within the above-described range and a mercaptocarboxylic acid in which the content of an inter-bimolecular condensed thioester compound is within the above-described range.

Here, an example of a factor of increasing the content of an intermolecular condensed thioester compound of a mercaptocarboxylic acid in the mercaptocarboxylic acid includes a method for storing the mercaptocarboxylic acid. In a case where iron is incorporated into the mercaptocarboxylic acid, the mercaptocarboxylic acid comes into contact with oxygen in the air, or the storage temperature of the mercaptocarboxylic acid increases, generation of the intermolecular condensed thioester compound of the mercaptocarboxylic acid is promoted. Accordingly, it is desirable that the mercaptocarboxylic acid is stored in a container, in which the contact with iron is avoided, in a state in which the storage temperature is kept low in a nitrogen atmosphere. For example, the suitable storage temperature is within a range of higher than or equal to 10° C. and lower than or equal to 60° C., more preferably within a range of higher than or equal to 15° C. and lower than or equal to 50° C., and still more preferably within a range of higher than or equal to 20° C. and lower than or equal to 40° C.

In addition, the content of an inter-bimolecular condensed thioester compound in a mercaptocarboxylic acid may be decreased through purification. The purification method is not particularly limited, but an example thereof includes purification performed through distillation.

Subsequently, a process for producing a pentaerythritol mercaptocarboxylic acid ester will be described.

[Process for Producing Pentaerythritol Mercaptocarboxylic Acid Ester]

In the present embodiment, it is possible to obtain a pentaerythritol mercaptocarboxylic acid ester by reacting pentaerythritol with a mercaptocarboxylic acid.

Acid catalysts represented by mineral acids such as a sulfuric acid, a hydrochloric acid, a phosphoric acid, and alumina or organic acids such as a p-toluenesulfonic acid, a benzenesulfonic acid, a methanesulfonic acid, a trichloroacetic acid, and a dibutyltin dioxide are preferably used as a generally used esterification catalyst for the reaction between pentaerythritol and a mercaptocarboxylic acid.

The preferred use ratio of pentaerythritol to a mercaptocarboxylic acid is not particularly limited. However, for example, the molar ratio of mercaptocarboxylic acid/pentaerythritol is within a range of 3.5 to 6.0, more preferably within a range of 3.7 to 5.0, and still more preferably within a range of 3.8 to 4.5. When the use ratio is within the above-described ranges, it is possible to efficiently produce a high purity pentaerythritol mercaptocarboxylic acid ester. The obtained pentaerythritol mercaptocarboxylic acid ester is colorless and transparent and tends to have a low viscosity. A polymerizable composition containing the pentaerythritol mercaptocarboxylic acid ester and a polyiso(thio)cyanate compound also tends to have a low viscosity. A resin obtained by curing the polymerizable composition also has a favorable color and tends to have qualities of excellent optical characteristics, heat resistance, or the like.

In addition, as the preferred conditions for the reaction between pentaerythritol and a mercaptocarboxylic acid, the temperature is, for example, within a range of 80° C. to 140° C. and more preferably within a range of 100° C. to 125° C. When the temperature is within the above-described ranges, the reaction between pentaerythritol and a mercaptocarboxylic acid is further promoted.

In addition, the obtained pentaerythritol mercaptocarboxylic acid ester is colorless and transparent, and tends to have a low viscosity. A polymerizable composition containing the pentaerythritol mercaptocarboxylic acid ester and a polyiso(thio)cyanate compound also tends to have a low viscosity. In addition, a resin obtained by curing the polymerizable composition also has a favorable color and tends to have qualities of excellent optical characteristics, heat resistance, or the like.

When producing a pentaerythritol mercaptocarboxylic acid ester, use of an azeotropic agent is not an essential condition. However, a method in which water which has been continuously by-produced is removed out of the system while performing heating and refluxing using an azeotropic agent is generally used. Examples of the azeotropic agent generally used include benzene, toluene, xylene, nitrobenzene, chlorobenzene, dichlorobenzene, anisole, diphenyl ether, methylene chloride, chloroform, and dichloroethane. These azeotropic agents may be used singly or in combination of two or more thereof. These azeotropic agents may be mixed with other solvents.

The pentaerythritol mercaptocarboxylic acid ester that can be obtained through the above-described method is not particularly limited as long as the pentaerythritol mercaptocarboxylic acid ester is a compound in which pentaerythritol and a mercaptocarboxylic acid are condensed, but examples thereof include the following compounds: a pentaerythritol thioglycolic acid ester, a pentaerythritol 3-mercaptopropionic acid ester, a pentaerythritol thiolactic acid ester, and a pentaerythritol thiosalicylic acid ester.

In addition, these ester compounds may be compounds in which a hydroxy group of pentaerythritol is completely or partially esterified.

Examples of the pentaerythritol mercaptocarboxylic acid ester preferably include pentaerythritol tetrakis(thioglycolate), pentaerythritol tetrakis(3-mercaptopropionate), pentaerythritol tetrakis(thiolactate), pentaerythritol tetrakis (thiosalicylate) and more preferably include pentaerythritol tetrakis (thioglycolate), pentaerythritol tetrakis(3-mercaptopropionate).

Furthermore, these ester compounds may be used singly or in combination of two or more thereof in a case of obtaining a polyurethane resin by polymerizing these ester compounds with polyiso(thio)cyanate compounds.

[Polymerizable Composition]

The polymerizable composition of the present embodiment contains a pentaerythritol mercaptocarboxylic acid ester obtained through the above-described production method and a polyiso(thio)cyanate compound.

The "iso(thio)cyanate" means "isocyanate or isothiocyanate".

Specific examples of the polyiso(thio)cyanate compound include: aliphatic polyisocyanate compounds such as hexamethylene diisocyanate, 2,2-dimethylpentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, bis(isocyanatoethyl)carbonate, bis(isocyanatoethyl)ether, lysine diisocyanatomethyl ester, and lysine triisocyanate; alicyclic polyisocyanate compounds such as 2,5-bis(isocyanatomethyl)-bicyclo[2.2.1]heptane, 2,6-bis(isocyanatomethyl)-bicyclo[2.2.1]heptane, bis(isocyanatomethyl)cyclohexane, dicyclohexylmethane diisocyanate, and isophorone diisocyanate; polyisocyanate compounds having aromatic ring compounds such as 1,2-diisocyanatobenzene, 1,3-diisocyanatobenzene, 1,4-diisocyanatobenzene, 2,4-diisocyanatotoluene, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluidine diisocyanate, 4,4'-methylenebis(phenyl isocyanate), 4,4'-methylenebis(2-methylphenyl isocyanate), bibenzyl-4,4'-diisocyanate, bis(isocyanatophenyl)ethylene, bis(isocyanatomethyl)benzene, bis(isocyanatoethyl)benzene, bis(isocyanatopropyl)benzene, α,α,α',α'-tetramethylxylylene diisocyanate, bis(isocyanatobutyl)benzene, bis(isocyanatomethyl)naphthalene, bis(isocyanatomethylphenyl)ether, bis(isocyanatoethyl)phthalate, and 2,6-di(isocyanatomethyl)furan; sulfur-containing aliphatic polyisocyanate compounds such as bis(isocyanatoethyl)sulfide, bis(isocyanatoethyl)sulfide, bis(isocyanatopropyl)sulfide, bis(isocyanatohexyl)sulfide, bis(isocyanatomethyl)sulfone, bis(isocyanatomethyl)disulfide, bis(isocyanatoethyl)disulfide, bis(isocyanatopropyl)disulfide, bis(isocyanatomethylthio)methane, bis(isocyanatoethylthio)methane, bis(isocyanatomethylthio)ethane, bis(isocyanatoethylthio)ethane, 1,5-diisocyanato-2-isocyanatomethyl-3-thiapentane, 1,2,3-tris(isocyanatomethylthio)propane, 1,2,3-tris(isocyanatoethylthio)propane, 3,5-dithia-1,2,6,7-heptane tetraisocyanate, 2,6-diisocyanatomethyl-3,5-dithia-1,7-heptane diisocyanate, 2,5-diisocyanatomethylthiophene, and 4-isocyanatoethylthio-2,6-dithia-1,8-octane diisocyanate; aromatic sulfide polyisocyanate compounds such as 2-isocyanatophenyl-4-isocyanatophenyl sulfide, bis(4-isocyanatophenyl)sulfide, and bis(4-isocyanatomethylphenyl)sulfide; aromatic disulfide polyisocyanate compounds such as bis(4-isocyanatophenyl)disulfide, bis(2-methyl-5-isocyanatophenyl)disulfide, bis(3-methyl-5-isocyanatophenyl)disulfide, bis(3-methyl-6-isocyanatophenyl)disulfide, bis(4-methyl-5-isocyanatophenyl)disulfide, and bis(4-methoxy-3-isocyanatophenyl)disulfide; sulfur-containing alicyclic polyisocyanate compounds such as 2,5-diisocyanatotetrahydrothiophene, 2,5-diisocyanatomethyltetrahydrothiophene, 3,4-diisocyanatomethyltetrahydrothiophene, 2,5-diisocyanato-1,4-dithiane, 2,5-diisocyanatomethyl-1,4-dithiane, 4,5-diisocyanato-1,3-dithiolane, 4,5-bis(isocyanatomethyl)-1,3-dithiolane, and 4,5-diisocyanatomethyl-2-methyl-1,3-dithiolane; aliphatic polyisothiocyanate compounds such as 1,2-diisothiocyanatoethane and 1,6-diisothiocyanatohexane; alicyclic polyisothiocyanate compounds such as cyclohexane diisothiocyanate; aromatic polyisothiocyanate compounds such as 1,2-diisothiocyanatobenzene, 1,3-diisothiocyanatobenzene, 1,4-diisothiocyanatobenzene, 2,4-diisothiocyanatotoluene, 2,5-diisothiocyanato-m-xylene, 4,4'-methylenebis(phenylisothiocyanate), 4,4'-methylenebis(2-methylphenylisothiocyanate), 4,4'-methylenebis(3-methylphenylisothiocyanate), 4,4'-diisothiocyanatobenzophenone, 4,4'-diisothiocyanato-3,3'-dimethylbenzophenone, and bis(4-isothiocyanatophenyl)ether; carbonyl polyisothiocyanate compounds such as 1,3-benzenedicarbonyl diisothiocyanate, 1,4-benzenedicarbonyl diisothiocyanate, and (2,2-pyridine)-4,4-dicarbonyl diisothiocyanate; sulfur-containing aliphatic polyisothiocyanate compounds such as thiobis(3-isothiocyanatopropane), thiobis(2-isothiocyanatoethane), and dithiobis(2-isothiocyanatoethane); sulfur-containing aromatic polyisothiocyanate compounds such as 1-isothiocyanato-4-[(2-isothiocyanato)sulfonyl]benzene, thiobis(4-isothiocyanatobenzene), sulfonyl(4-isothiocyanatobenzene), and dithiobis(4-isothiocyanatobenzene); sulfur-containing alicyclic polyisothiocyanate compounds such as 2,5-diisothiocyanatothiophene and 2,5-diisothiocyanato-1, 4-dithiane; and polyiso(thio)cyanate compounds such as 1-isocyanato-6-isothiocyanatohexane, 1-isocyanato-4-isothiocyanatocyclohexane, 1-isocyanato-4-isothiocyanatobenzene, 4-methyl-3-isocyanato-1-isothiocyanatobenzene, 2-isocyanato-4,6-diisothiocyanato-1,3,5-triazine, 4-isocyanatophenyl-4-isothiocyanatophenyl sulfide, and 2-isocyanatoethyl-2-isothiocyanatoethyl disulfide, which have isocyanato group and a isothiocyanato group.

Furthermore, it is also possible to use halogen-substituted products such as a chlorine-substituted product or a bromine-substituted product, an alkyl-substituted product, an alkoxy-substituted product, a nitro-substituted product, a prepolymer type-modified product with a polyhydric alcohol, a carbodiimide-modified product, a urea-modified product, a burette-modified product, a dimerization or trimerization reaction product, and the like. These compounds may be used singly or in combination of two or more thereof.

In the present embodiment, the polymerizable composition may contain other thiol compounds or polyol compounds than the pentaerythritol mercaptocarboxylic acid ester. Here, a thiol compound having a hydroxy group in an identical molecule is included in the thiol compound.

Examples of the other thiol compounds include aliphatic polythiol compounds such as methanedithiol, 1,2-ethanedithiol, 1,2,3-propanetrithiol, 1,2-cyclohexanedithiol, bis(2-mercaptoethyl)ether, tetrakis(mercaptomethyl)methane, diethylene glycol bis(2-mercaptoacetate), diethylene glycol bis(3-mercaptopropionate), ethylene glycol bis (2-mercaptoacetate), ethylene glycol bis(3-mercaptopropionate), trimethylolpropane tris(2-mercaptoacetate), trimethylolpropane tris(3-mercaptopropionate), trimethylolethane tris(2-mercaptoacetate), trimethylolethane tris(3-mercaptopropionate), pentaerythritol bis(3-mercaptopropionate), pentaerythritol tris(3-mercaptopropionate), 2-hydroxymethyl-2-(((3-((3-mercaptopropanoyl)thio)propanoyl)oxy) methyl)propane-1, 3-diylbis(3-mercaptopropionate), 2-(((3-mercaptopropanoyl)oxy)methyl)-2-(((3-((3-mercaptopropanoy l)thio)propanoyl)oxy)methyl)propane-1,3-diylbis(3-mercaptopropionate), formalin condensate of pentaerythritol tetrakis(3-mercaptopropionate), bis(mercaptomethyl)sulfide, bis(mercaptomethyl)disulfide, bis(mercaptoethyl)sulfide, bis(mercaptoethyl)disulfide, bis(mercaptopropyl)sulfide, bis(mercaptomethylthio)methane, bis(2-mercaptoethylthio)methane, bis(3-mercaptopropylthio) methane, 1,2-bis(mercaptomethylthio)ethane, 1,2-bis(2-mercaptoethylthio)ethane, 1,2-bis(3-mercaptopropylthio)ethane, 1,2,3-tris(mercaptomethylthio)propane, 1,2,3-tris(2-mercaptoethylthio)propane, 1,2,3-tris(3-mercaptopropylthio)propane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1, 11-dimercapto-3,6,9-trithiaundecane, 4,8-dimercaptomethyl-1,11-dimercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, 2,5-dimercaptomethyl-1,4-dithiane, 2,5-dimercapto-1,4-dithiane, 2,5-dimercaptomethyl-2,5-dimethyl-1,4-dithiane, and esters of thioglycolic acids and mercaptopropionic acids thereof, hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxymethyl disulfide bis(2- mercaptoacetate), hydroxymethyl disulfide bis(3-mercaptopropionate), hydroxyethyl disulfide bis(2-mercaptoacetate), hydroxyethyl disulfide bis(3-mercaptopropinate), 2-mercaptoethyl ether bis(2-mercaptoacetate), 2-mercaptoethyl ether bis(3-mercaptopropionate), thiodiglycolic acid bis(2-mercaptoethyl ester), thiodipropionic acid bis(2-mercaptoethyl ester), dithiodiglycolic acid bis(2-mercaptoethyl ester), dithiodipropionic acid bis(2-mercaptoethyl ester), 1,1,3,3-tetrakis(mercaptomethylthio)propane, 1,1,2,2-tetrakis(mercaptomethylthio)ethane, 4,6-bis(mercaptomethylthio)-1,3-dithiane, tris(mercaptomethylthio)methane, and tris(mercaptoethylthio)methane; aromatic polythiol compounds such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,3,5-trimercaptobenzene, 1,3,5-tris(mercaptomethyl)benzene, 1,3,5-tris(mercaptomethyleneoxy)benzene, 1,3,5-tris(mercaptoethyleneoxy)benzene, 2,5-toluenedithiol, 3,4-toluenedithiol, 1,5-naphthalenedithiol, and 2,6-naphthalenedithiol; and heterocyclic polythiol compounds such as 2-methylamino-4,6-dithiol-sym-triazine, 3,4-thiophenedithiol, bismuthiol, 4,6-bis(mercaptomethylthio)-1,3-dithiane, and 2-(2,2-bis(mercaptomethylthio)ethyl)-1,3-dithietane.

Examples of the thiol compound having a hydroxy group in an identical molecule include 2-mercaptoethanol, 3-mercapto-1,2-propanediol, 4-mercaptophenol, and 2,3-dimercapto-1-propanol, but the present invention is not limited to these exemplified compounds.

Examples of the polyol compounds include aliphatic polyols such as ethylene glycol, diethylene glycol, polyethylene glycol, propylene glycol, dipropylene glycol, tripropylene glycol, polypropylene glycol, butylene glycol, neopentyl glycol, glycerin, trimethylolethane, trimethylolpropane, ditrimethylolpropane, butanetriol, 1,2-methyl glucoside, pentaerythritol, dipentaerythritol, tripentaerythritol, sorbitol, erythritol, threitol, ribitol, arabinitol, xylitol, allitol, mannitol, dulcitol, iditol, glycol, inositol, hexanetriol, triglycerol, diglycerol, triethylene glycol, polyethylene glycol, tris(2-hydroxyethyl)isocyanurate, cyclobutanediol, cyclopentanediol, cyclohexanediol, cycloheptanediol, cyclooctanediol, cyclohexanedimethanol, hydroxypropylcyclohexanol, tricyclo[5.2.1.0$^{2,6}$]decane-dimethanol, bicyclo[4,3,0]-nonanediol, dicyclohexanediol, tricyclo[5,3,1,1]dodecanediol, bicyclo[4,3,0]nonanedimethanol, tricyclo[5,3,1,1]dodecane-diethanol, hydroxypropyl tricyclo[5,3,1,1]dodecanol, spiro[3,4]octanediol, butylcyclohexanediol, 1,1'-bicyclohexylidenediol, cyclohexanetriol, maltitol, and lactose; aromatic polyols such as dihydroxynaphthalene, trihydroxynaphthalene, tetrahydroxynaphthalene, dihydroxybenzene, benzenetriol, biphenyltetraol, pyrogallol, (hydroxynaphthyl)pyrogallol, trihydroxyphenanthrene, bisphenol A, bisphenol F, xylylene glycol, di(2-hydroxyethoxy)benzene, bisphenol A-bis-(2-hydroxyethyl ether), tetrabromobisphenol A, and tetrabromobisphenol A-bis-(2-hydroxyethyl ether); halogenated polyols such as dibromoneopentyl glycol; and polymer polyols such as an epoxy resin. In the present embodiment, at least one selected from these compounds can be used in combination.

In addition, examples of other polyol compounds include condensation reaction products of the above-described polyols and organic acids such as an oxalic acid, a glutamic acid, an adipic acid, an acetic acid, a propionic acid, a cyclohexane carboxylic acid, a β-oxocyclohexane propionic acid, a dimer acid, a phthalic acid, an isophthalic acid, a salicylic acid, a 3-bromopropionic acid, 2-bromoglycol, dicarboxycyclohexane, a pyromellitic acid, a butanetetracarboxylic acid, and a bromophthalic acid; addition reaction products of the above-described polyols and alkylene oxides such as ethylene oxide or propylene oxide; addition reaction products of alkylene polyamine and alkylene oxides such as ethylene oxide or propylene oxide; bis-[4-(hydroxyethoxy)phenyl]sulfide, bis-[4-(2-hydroxypropoxy)phenyl]sulfide, bis-[4-(2,3-dihydroxypropoxy)phenyl]sulfide, bis-[4-(4-hydroxycyclohexyloxy)phenyl]sulfide, bis-[2-methyl-4-(hydroxyethoxy)-6-butylphenyl]sulfide, and compounds obtained by adding an average of 3 or less molecules of ethylene oxide and/or propylene oxide per hydroxyl group to those compounds; and polyols, such as di-(2-hydroxyethyl)sulfide, 1,2-bis-(2-hydroxyethylmercapto)ethane, bis(2-hydroxyethyl)disulfide, 1,4-dithiane-2,5-diol, bis(2,3-dihydroxypropyl)sulfide, tetrakis(4-hydroxy-2-thiabutyl)methane, bis(4-hydroxyphenyl)sulfone (trade name: BISPHENOL S), tetrabromobisphenol S, tetramethyl bisphenol S, 4,4'-thiobis(6-tert-butyl-3-methylphenol), and 1,3-bis(2-hydroxyethylthioethyl)-cyclohexane, which contain a sulfur atom. In the present embodiment, at least one selected from these compounds can be used in combination.

[Resin]

It is possible to obtain a resin by curing a polymerizable composition which contains the pentaerythritol mercaptocarboxylic acid ester obtained as described above and a polyiso(thio)cyanate compound, and other polythiol compounds that can be contained as necessary.

Here, the use ratio of the pentaerythritol mercaptocarboxylic acid ester, the polyiso(thio)cyanate compound, and the other polythiol compounds that can be contained as necessary is not particularly limited. However, the molar ratio of SH group/NCO group (or NCS group) is within a range of 0.3 to 2.0, preferably within a range of 0.7 to 2.0, and more preferably within a range of 0.8 to 1.3. When the molar ratio is within the above-described range, a molded product formed of the resin obtained by curing a polymerizable composition has a favorable color and qualities of excellent optical characteristics, heat resistance, or the like.

In addition, other substances may be added to the resin of the present embodiment in addition to the ester compound and the iso(thio)cyanate compound which form the resin for the purpose of improving physical properties, operability, polymerization reactivity, and the like of the resin. For example, one, two or more kinds of an active hydrogen compound represented by an amine, an epoxy compound, an olefin compound, a carbonate compound, an ester compound, metal, metal oxide, an organometallic compound, and an inorganic substance may be added to the resin in addition to the iso(thio)cyanate compound.

In addition, various substances such as a chain extender, a crosslinking agent, a light stabilizer, an ultraviolet absorber, an antioxidant, an oil-soluble dye, a filler, a release agent, and a bluing agent may be added thereto similarly to a well-known molding method in accordance with the purpose. A well-known reaction catalyst used for producing a thiocarbamic acid S-alkyl ester, a polyurethane or polythiourethane resin may be appropriately added thereto in order to adjust a desired reaction rate. In addition, in the present embodiment, it is also possible to perform a polymerization reaction by partially adding other polythiol compounds to a polymerizable composition in addition to the pentaerythritol mercaptocarboxylic acid ester obtained through the above-described production method.

In addition, a lens formed of the resin of the present embodiment can usually be obtained through cast polymerization.

Specifically, a pentaerythritol mercaptocarboxylic acid ester and a polyiso(thio)cyanate compound, and other polythiol compounds that can be contained as necessary are mixed with each other. This mixture is degassed through an appropriate method as necessary. Then, the degassed mixture is injected into a mold and polymerization is performed while gradually heating the mixture generally from a low temperature to a high temperature.

The molded product formed of the resin of the present embodiment which can be obtained in this manner has characteristics of high refractive index and low dispersion, and characteristics of excellent color, heat resistance, durability, and impact resistance, and has a light weight. Furthermore, the molded product is colorless and transparent since the generation of cloudiness is suppressed. The color of the resin molded product of the present embodiment can be represented by a yellow index (Y.I.). The Y.I. of the resin molded product of the present embodiment is 4 or less, preferably 3.6 or less, and more preferably 3.3 to 3.6, which indicates an excellent color.

For this reason, the molded product formed of the resin can be suitably used as optical materials of lenses such as a spectacle lens and a camera lens, and other light emitting diodes.

In addition, physical and chemical treatments such as surface polishing, an antistatic treatment, hard coating treatment, non-reflective coating treatment, dyeing treatment, and dimming treatment may be performed on the resin molded product of the present embodiment in order to achieve an improvement in such as antireflection, provision of high hardness, improvement in abrasion resistance and chemical resistance, provision of anti-fogging properties, or provision of fashionability as necessary.

In the above, the embodiment of the present invention has been described. However, the embodiment is merely an example of the present invention, and various configurations other than those described above can be employed.

EXAMPLES

Subsequently, the present invention will be described in detail using examples. In the following examples and a comparative example, pentaerythritol was analyzed through the following method.

In addition, the color (Y.I.) of the obtained pentaerythritol mercaptocarboxylic acid ester, and the color (Y.I.) and the transparency (loss degree of transparency) of the polythiourethane resin molded product obtained by polymerizing a polymerizable composition were evaluated through the following test method.

Content of bispentaerythritol: After dissolving pentaerythritol in water, the aqueous solution was subjected to high-performance liquid chromatography and the content of bispentaerythritol was measured.

Contents of sodium and calcium: After dissolving pentaerythritol in water, the aqueous solution was subjected to high-performance liquid ion chromatography and the contents of sodium and calcium were measured.

Absorbance of pentaerythritol aqueous solution: Distilled water was added to 2 parts by weight of pentaerythritol to make 40 parts by weight. Then, the aqueous solution was dissolved while being heated to a temperature of 60° C. to obtain a 5 wt % pentaerythritol aqueous solution. The aqueous solution was cooled to 20° C. and filtered using a 0.45 µm filter to obtain a measurement sample.

Next, a quartz cell having an optical path length of 50 mm was filled with the measurement sample solution and the absorbance at a wavelength of 270 nm was obtained using a spectrophotometer (equipment name: UV-1600) manufactured by Shimadzu Corporation.

Yellow index (Y.I.) of pentaerythritol mercaptocarboxylic acid ester: Y.I. was employed as an analysis item for evaluating a color of a pentaerythritol mercaptocarboxylic acid ester. A correlation that the color of the pentaerythritol mercaptocarboxylic acid ester is further improved as the Y.I. value becomes smaller and the color of the pentaerythritol mercaptocarboxylic acid ester is further deteriorated as the Y.I. value becomes larger is obtained. More specifically, a tristimulus value Y and chromaticity coordinates x and y of a CIE-1391 color system were measured using COLOR-DIFFERENCE METER CT-210 manufactured by MINOLTA. First, distilled water was placed in a cell CT-A20 having an optical path length of 20 mm and white calibration was performed while setting Y as 100.00, x as 0.3101, and y as 0.3162. Thereafter, the sample was placed in the same cell to perform color measurement. The Y.I. was calculated using the following Formula based on the values of x and y which were measurement results.

$$Y.I.=(234*x+106*y+106)y \quad (1)$$

Yellow index (Y.I.) of polythiourethane resin molded product: Y.I. was employed as an analysis item for evaluating a color of a plastic lens containing a polythiourethane resin. A correlation that the color of the plastic lens is further improved as the Y.I. value becomes smaller and the color of the plastic lens is further deteriorated as the Y.I. value becomes larger is obtained. A circular flat plastic lens having a thickness of 9 mm and ϕ 75 mm was prepared and chromaticity coordinates x and y were measured using COLOR-DIFFERENCE METER CT-210 manufactured by MINOLTA. The Y.I. was calculated using Formula (1) based on the values of x and y which were measurement results.

Devitrification degree: The devitrification degree was employed as an analysis item for evaluating the transparency of the plastic lens containing a polythiourethane resin. The devitrification degree was obtained through the following procedure. A circular flat lens plate with a thickness of 9 mm and ϕ 75 mm was prepared. Next, the lens plate was irradiated with a light source (Luminar Ace LA-150A manufactured by HAYASHI) and measurement was performed using a gray scale image device. A captured image was digitized through gray scale image processing to obtain the devitrification degree.

Example 1

Synthesis of Pentaerythritol Tetrakis(3-Mercaptopropionate)

641.5 parts by weight (6.00 mol) of a 3-mercaptopropionic acid with a purity of 99.7% which contains 0.2% (area percentage) of a 3-(3-mercaptopropanoylthio)propionic acid, 214.6 g (1.5 mol) of pentaerythritol with a purity of 95.2% which contains 4.7 wt % of bispentaerythritol, 0.1 wt % of sodium, and 0.02 wt % of calcium, 5.7 g of p-toluenesulfonic acid monohydrate, and 278.3 g of toluene were added into a 2 liter four-necked reaction flask equipped with a stirrer, a reflux cooling water separator, a nitrogen gas purge tube, and a thermometer. The absorbance at a wavelength of 270 nm of a 5 wt % aqueous solution of the pentaerythritol used was 0.032. Subsequently, water which was produced as a by-product while performing heating and refluxing was continuously distilled out of the system and a reaction was performed for 7.0 hours (at internal temperature of 96° C. to 121° C.). Then, the reaction solution was cooled to a room temperature. The amount of water taken out of the system was 99.3% with respect to theoretically produced water. The reaction solution was washed with a base and was then washed with water. Toluene and a trace amount of moisture were removed while heating under reduced pressure. Thereafter, filtration was performed and the obtained product was identified. As a result, 716.8 g of pentaerythritol tetrakis(3-mercaptopropionate) was obtained. The Y.I. of the obtained pentaerythritol tetrakis(3-mercaptopropionate) was 0.9.

(Production of Plastic Lens (Resin Molded Body))

A flask which had been sufficiently dried was accurately filled with 0.042 g of dibutyltin dichloride, 0.084 g of ZELEC UN (trade name, acidic phosphoric ester manufactured by Stepan), and 0.07 g of BIOSORB 583 (trade name, ultraviolet absorber manufactured by KYODO CHEMICAL CO., LTD.), and then, was filled with 35.4 g of 2,5(6)-bis (isocyanatomethyl)-bicyclo[2.2.1]heptane as an isocyanate compound. The mixture was dissolved while being stirred for 1 hour at 25° C. Thereafter, the flask was filled with 16.7 g of pentaerythritol tetrakis(3-mercaptopropionate) which had been synthesized through the above-described method and 17.9 g of 4-mercaptomethyl-1,8-dimercapto-3,6-dithiaoctane as thiol compounds which were then mixed with the formulation to make a uniform polymerizable composition before polymerization.

This polymerizable composition before polymerization was degassed for 1 hour at 600 Pa and was then filtered using 3 μm PTFE filter. Thereafter, the polymerizable composition was injected into a mold formed of a glass mold and tape. This mold was placed in an oven and the temperature of the oven was gradually increased from 10° C. to 120° C. to perform polymerization for 18 hours. After the completion of the polymerization, the mold was taken out of the oven and released from the mold to obtain a resin molded product. The obtained resin molded product was further subjected to annealing for 4 hours at 130° C. In the obtained resin molded product, the Y.I. was 3.5 and the devitrification degree representing the transparency was 19.

The analysis results of raw materials used and the evaluation results of the obtained plastic lens are shown in Table 1.

Example 2

Pentaerythritol tetrakis(3-mercaptopropionate) was synthesized similarly to Example 1 except that pentaerythritol with a purity of 95.2% which contained 4.7 wt % of bispentaerythritol, 0.1 wt % of sodium, and 0.01 wt % of calcium and of which the absorbance at a wavelength of 270 nm of a 5 wt % aqueous solution was 0.011 was used instead of the pentaerythritol used in Example 1. The Y.I. of the obtained pentaerythritol tetrakis(3-mercaptopropionate) was 1.0. A plastic lens was produced similarly to Example 1 using the obtained pentaerythritol tetrakis(3-mercaptopropionate). The analysis results of raw materials used and the evaluation results of the obtained plastic lens are shown in Table 1.

Example 3

Pentaerythritol tetrakis(3-mercaptopropionate) was synthesized similarly to Example 1 except that pentaerythritol with a purity of 95.2% which contained 4.7 wt % of bispentaerythritol, 0.1 wt % of sodium, and 0.03 wt % of calcium and of which the absorbance at a wavelength of 270 nm of a 5 wt % aqueous solution was 0.06 was used instead of the pentaerythritol used in Example 1. The Y.I. of the obtained pentaerythritol tetrakis(3-mercaptopropionate) was 0.9. A plastic lens was produced similarly to Example 1 using the obtained pentaerythritol tetrakis(3-mercaptopropionate). The analysis results of raw materials used and the evaluation results of the obtained plastic lens are shown in Table 1.

Example 4

A flask which had been sufficiently dried was accurately filled with 0.0035 g of dibutyltin dichloride, 0.063 g of ZELEC UN (trade name, acidic phosphoric ester manufactured by Stepan), and 0.035 g of BIOSORB 583 (trade name, ultraviolet absorber manufactured by KYODO CHEMICAL CO., LTD.), and then, was filled with 30.5 g of m-xylylene diisocyanate. The mixture was mixed and dissolved at 20° C. Thereafter, the flask was filled with 39.5 g of pentaerythritol tetrakis(3-mercaptopropionate) synthesized through the method described in Example 1 which was then mixed with the formulation to make a uniform polymerizable composition before polymerization.

This polymerizable composition before polymerization was degassed for 1 hour at 600 Pa and was then filtered using 3 μm PTFE filter. Thereafter, the polymerizable composition was injected into a mold formed of a glass mold and tape. This mold was placed in an oven and the temperature of the oven was gradually increased from 10° C. to 120° C. to perform polymerization for 18 hours. After the completion of the polymerization, the mold was taken out of the oven and released from the mold to obtain a resin molded product. The obtained resin molded product was further subjected to annealing for 4 hours at 130° C. In the obtained resin molded product, the Y.I. was 3.6 and the devitrification degree representing the transparency was 20.

Example 5

A resin molded product was produced similarly to Example 1 except that in the production of the plastic lens (resin molded product), 16.7 g of a mixture of pentaerythritol di(3-mercaptopropionate), pentaerythritol tris(3-mercaptopropionate), 2-hydroxymethyl-2-(((3-((3-mercaptopropanoyl)thio)propanoyl)oxy) methyl)propane-1,3-diylbis (3-mercaptopropionate), 2-(((3-mercaptopropanoyl)oxy) methyl)-2-(((3-((3-mercaptopropanoy l)thio)propanoyl) oxy)methyl)propane-1,3-diylbis(3-mercaptopropionate), formalin condensate of pentaerythritol tetrakis(3-mercaptopropionate), and pentaerythritol tetrakis(3-mercaptopropionate), and 17.9 g of 4-mercaptomethyl-1,8-dimercapto-3, 6-dithiaoctane were used as thiol compounds. The resin molded product having the same physical properties of a resin as those of Example 1 was obtained.

Comparative Example 1

Pentaerythritol tetrakis(3-mercaptopropionate) was synthesized similarly to Example 1 except that pentaerythritol with a purity of 95.2% which contained 4.7 wt % of bispentaerythritol, 0.1 wt % of sodium, and 0.03 wt % of calcium and of which the absorbance at a wavelength of 270 nm of a 5 wt % aqueous solution was 0.091 was used instead of the pentaerythritol used in Example 1. The Y.I. of the obtained pentaerythritol tetrakis(3-mercaptopropionate) was 1.5. A plastic lens was produced similarly to Example 1 using the obtained pentaerythritol tetrakis(3-mercaptopropionate). The analysis results of raw materials used and the evaluation results of the obtained plastic lens are shown in Table 1.

TABLE 1

|  |  |  | Example 1 | Example 2 | Example 3 | Example 4 | Comparative Example 1 |
|---|---|---|---|---|---|---|---|
| Raw material | 3-Mercaptopropionic acid | Purity [%] | 99.7 | 99.7 | 99.7 | 99.7 | 99.7 |
|  |  | Content of 3-(3-mercaptopropanoylthio)propionic acid [%] (area percentage) | 0.2 | 0.2 | 0.2 | 0.2 | 0.2 |
|  | Pentaerythritol | Purity [%] | 95.2 | 95.2 | 95.2 | 95.2 | 95.2 |
|  |  | Absorbance | 0.032 | 0.011 | 0.06 | 0.032 | 0.091 |
|  |  | Content of bispentaerythritol [wt %] | 4.7 | 4.7 | 4.7 | 4.7 | 4.7 |
|  |  | Content of sodium [wt %] | 0.1 | 0.1 | 0.1 | 0.1 | 0.1 |
|  |  | Content of calcium [wt %] | 0.02 | 0.01 | 0.03 | 0.02 | 0.03 |
| Product | Pentaerythritol tetrakis(3-mercaptopropionate) | Y.I. | 0.9 | 1.0 | 0.9 | 0.9 | 1.5 |
| Reactant | Other thiol compound |  | *1 | *1 | *1 | — | *1 |
|  | Polyisocyanate compound |  | *2 | *2 | *2 | *3 | *2 |
| Resin | Y.I. |  | 3.5 | 3.3 | 3.6 | 3.6 | 3.7 |
|  | Devitrification degree |  | 19 | 19 | 20 | 20 | 21 |

*1: 4-mercaptomethyl-1,8-dimercapto-3,6-dithiaoctane
*2: 2,5(6)-bis(isocyanatomethyl)-bicyclo[2.2.1]heptane
*3: m-xylylene diisocyanate From the results shown in Table 1, it is possible to improve the Y.I. of an ester product to be obtained, by using pentaerythritol in which the absorbance of a 5 wt % aqueous solution of pentaerythritol at a wavelength of 270 nm is a specific value or less. Furthermore, even in a case where a resin is prepared using this ester product, it is possible to improve optical characteristics of the resin.

According to the process for producing a pentaerythritol mercaptocarboxylic acid ester of the present invention, it is possible to provide a pentaerythritol mercaptocarboxylic acid ester which allows a resin molded product having an excellent appearance such as a color to be obtained.

This pentaerythritol mercaptocarboxylic acid ester provides a resin having excellent appearance or the like, and therefore, is effective for producing various optical materials.

Priority is claimed on Japanese Patent Application No. 2015-126417, filed on Jun. 24, 2015, the content of which is incorporated herein by reference.

The invention claimed is:

1. A process for producing a pentaerythritol mercaptocarboxylic acid ester, the method comprising:
   a step of reacting pentaerythritol with a mercaptocarboxylic acid to obtain a pentaerythritol mercaptocarboxylic acid ester,
   wherein an absorbance of a 5 wt % aqueous solution of the pentaerythritol at a wavelength of 270 nm, which is measured using a quartz cell having an optical path length of 50 mm, is 0.003 or more and 0.07 or less,
   the content of bispentaerythritol in the pentaerythritol, with respect to the total weight of the pentaerythritol, is 1 wt % to 5 wt %, and
   the content of Na and Ca in the pentaerythritol, with respect to the total weight of the pentaerythritol, is less than 1 wt %.

2. The process for producing a pentaerythritol mercaptocarboxylic acid ester according to claim 1,
   wherein the mercaptocarboxylic acid is a 3-mercaptopropionic acid or a thioglycolic acid.

3. A polymerizable composition comprising:
   the pentaerythritol mercaptocarboxylic acid ester obtained through the production method according to claim 1; and
   a polyiso(thio)cyanate compound.

4. A resin obtained by curing the polymerizable composition according to claim 3.

5. An optical material composed of the resin according to claim 4.

6. A lens composed of the resin according to claim 4.

* * * * *